United States Patent
Rioux et al.

(10) Patent No.: US 8,221,417 B2
(45) Date of Patent: Jul. 17, 2012

(54) DISPOSABLE ELECTRO-SURGICAL COVER ELEMENTS AND ELECTRO-SURGICAL INSTRUMENT

(75) Inventors: Robert F. Rioux, Ashland, MA (US); Kathleen Kane, Brookline, MA (US); Devon Berman, Loudon, NH (US)

(73) Assignee: Boston Scientific Scimed, Inc., Maple Grove, MA (US)

( * ) Notice: Subject to any disclaimer, the term of this patent is extended or adjusted under 35 U.S.C. 154(b) by 881 days.

(21) Appl. No.: 12/269,809

(22) Filed: Nov. 12, 2008

(65) Prior Publication Data

US 2009/0125012 A1 May 14, 2009

Related U.S. Application Data

(60) Provisional application No. 60/987,727, filed on Nov. 13, 2007.

(51) Int. Cl.
*A61B 18/18* (2006.01)
(52) U.S. Cl. .......................................... 606/51
(58) Field of Classification Search ............ 606/41, 606/51, 52
See application file for complete search history.

(56) References Cited

U.S. PATENT DOCUMENTS

| | | |
|---|---|---|
| 3,503,398 A | 3/1970 | Fogarty et al. |
| 4,763,669 A | 8/1988 | Jaeger |
| 5,584,845 A | 12/1996 | Hart |
| 5,951,549 A | 9/1999 | Richardson et al. |
| 6,050,996 A | 4/2000 | Schmaltz et al. |
| 6,277,117 B1 | 8/2001 | Tetzlaff et al. |
| 6,334,861 B1 | 1/2002 | Chandler et al. |
| 7,232,440 B2 | 6/2007 | Dumbauld et al. |
| 7,270,664 B2 | 9/2007 | Johnson et al. |
| 7,276,068 B2 | 10/2007 | Johnson et al. |
| 7,367,976 B2 | 5/2008 | Lawes et al. |
| 2003/0144652 A1 | 7/2003 | Baker et al. |
| 2003/0158549 A1 | 8/2003 | Swanson |
| 2004/0006340 A1 | 1/2004 | Latterel et al. |
| 2005/0112521 A1 | 5/2005 | Harvey et al. |

(Continued)

FOREIGN PATENT DOCUMENTS

EP 1 287 788 A1 3/2003

(Continued)

OTHER PUBLICATIONS

PCT International Preliminary Report on Patentability (Chapter I of the Patent Cooperation Treaty) for PCT/US2008/083276, Applicant: Boston Scientific Scimed, Inc., Form PCT/IB/326 and 373, dated May 27, 2010 (7 pages).

(Continued)

*Primary Examiner* — Nicholas Lucchesi
*Assistant Examiner* — Nathan R Price
(74) *Attorney, Agent, or Firm* — Vista IP Lawgroup LLP

(57) ABSTRACT

Electro-surgical instrument and attachments for converting a mechanical surgical instrument into an electro-surgical instrument are disclosed for applying electrical current to tissue, such as a blood vessel, to seal or cauterize the tissue. A cover element is slidable over a distal end of a component of a mechanical surgical instrument, such as a forceps. Each cover element defines a single pocket or cavity and a single aperture or opening at one end thereof for receiving and surrounding the distal end of the component and an electrically conductive element attached to an outer surface of the cover element. RF energy can be applied to tissue through the electrically conductive elements. After the procedure, the cover elements can be slidably removed from the forceps member and are disposable.

25 Claims, 12 Drawing Sheets

U.S. PATENT DOCUMENTS

| | | |
|---|---|---|
| 2005/0154387 A1 | 7/2005 | Moses et al. |
| 2006/0064086 A1 | 3/2006 | Odom |
| 2009/0138003 A1 | 5/2009 | Deville et al. |

FOREIGN PATENT DOCUMENTS

| | | |
|---|---|---|
| EP | 1 532 933 A1 | 5/2005 |
| EP | 1 769 765 A1 | 4/2007 |
| WO | WO 01/66026 A2 | 9/2001 |
| WO | WO 01/66026 A3 | 9/2001 |
| WO | WO 02/24089 A1 | 3/2002 |
| WO | WO 03/020339 A2 | 3/2003 |
| WO | WO 03/020339 A3 | 3/2003 |

OTHER PUBLICATIONS

PCT International Preliminary Report on Patentability (Chapter I of the Patent Cooperation Treaty) for PCT/US2008/083270, Applicant: Boston Scientific Scimed, Inc., Form PCT/IB/326 and 373, dated May 27, 2010 (8 pages).

PCT International Search Report for PCT/US2008/083276, Applicant: Boston Scientific Scimed, Inc., Form PCT/ISA/210 and 220, dated Feb. 18, 2009 (6 pages).

PCT Written Opinion of the International Search Authority for PCT/US2008/083276, Applicant: Boston Scientific Scimed, Inc., Form PCT/ISA/237, dated Feb. 18, 2009 (5 pages).

PCT International Search Report for PCT/US2008/083270, Applicant: Boston Scientific Scimed, Inc., Form PCT/ISA/210 and 220, dated Mar. 23, 2009 (8 pages).

PCT Written Opinion of the International Search Authority for PCT/US2008/083270, Applicant: Boston Scientific Scimed, Inc., Form PCT/ISA/237, dated Mar. 23, 2009 (6 pages).

LigaSure Product Brochure, www.ligasure.com/pdf/prod_info/lsligasurevss.pdf (dated Sep. 2004).

Office Communication dated Jun. 22, 2010 in European Patent Application No. 08848871.3-1265 (1 page).

Response to Office Communication dated Aug. 2, 2010 in European Patent Application No. 08848871.3-1269 (12 page).

DISPOSABLE ELECTRO-SURGICAL COVER ELEMENTS AND ELECTRO-SURGICAL INSTRUMENT

RELATED APPLICATION

This Application claims priority to U.S. Provisional Patent Application No. 60/987,727 filed on Nov. 13, 2007. The '727 Application is incorporated by reference as if set forth fully herein.

FIELD OF INVENTION

The present inventions relate to electro-surgical devices and, more particularly, to disposable attachments for converting mechanical surgical instruments into electro-surgical instruments.

BACKGROUND

Referring to FIG. 1, a forceps 10 is a known mechanical surgical instrument or device that is used to grasp or hold tissue, such as a blood vessel (BV) (generally "blood vessel"). A typical forceps 10 includes first and second shafts or elongated members 20a and 20b (generally 20) that are connected at and rotatably moveable about a connection point or pivot 24. First and second handles 30a and 30b (generally 30) at proximal ends 34a and 34b (generally 34) of the forceps 10 can be manipulated by a surgeon to move the first and second members 20a and 20b, thereby opening and closing jaw or clamping members 40a and 40b (generally 40) at the distal ends 44a and 44b (generally 44) of the forceps 10 to release and grasp the blood vessel. A forceps 10 may include interlocking ratchets 50a and 50b (generally 50) to lock the position of the members 20a and 20b and jaws 40a and 40b. Inner faces or surfaces 41a and 41b (generally 41) of respective jaws 40a and 40b contact a blood vessel can be straight or have a needle-nose like shape (as shown in FIG. 2) and can also have a curved shape (as shown in FIG. 3). A contact surface 41 of a jaw 40 may have a grooved or ridged surface 60 in order to more securely grasp the blood vessel there between.

Referring to FIG. 4, it is known to apply electrical current (C) to a forceps 10 in order to coagulate, cauterize or seal a blood vessel that is held between the jaws 40. Cauterization involves burning or necrosing the vessel by rupturing and drying the vessel tissue. Sealing a blood vessel involves liquefying collagen in the vessel tissue so that it reforms or fuses into a mass, which prevents blood from passing through the vessel.

One known method of applying electrical current to a blood vessel using a forceps 10 is to contact or tap a forceps handle 30 or shaft member 20 with a wire, lead or electrode 72. The electrode 72 is coupled to a source of electrical current 70, such as a radio frequency or RF generator or other suitable power source (generally RF generator). Electrical current conducts from the RF generator, through the forceps 10, and to the blood vessel whenever the RF generator 70 is active and a surgeon brings the electrode 72 in contact with the forceps 10.

While known "tap" devices and techniques have been used in the past with some effectiveness, they can be improved. For example, as shown in FIG. 4, when the electrode 72 is brought into contact with the forceps 10, electrical current conducts through all of the conductive forceps 10 components within a conductive path. Thus, electrical current may conduct through the handles 30, the shaft members 20, the jaws 40 and then to the blood vessel to be treated. As a result, current is applied "globally," i.e., to the blood vessel and also to tissue surrounding the forceps 10. Thus, such devices and techniques do not apply current "locally" to a selected region at a distal end 44 of a jaw 40 that holds the blood vessel to be treated.

Thus, with known "contact" or "tap" devices and techniques, larger currents must be applied to the forceps 10 to compensate for current that is conducted to surrounding tissue in order to achieve desired cauterization or sealing results at the target vessel held by the jaws members 40. Additionally, vessel engaging surfaces 48 are permanent or integrally formed components and, therefore, cannot be removed or replaced after a procedure. Consequently, jaw members 40 must be sterilized after each use, which is costly, time consuming and inconvenient. Further, jaw members 40 may be damaged during use. Damaged jaw members 40 may result in inconsistent cauterization and sealing when the same forceps 10 are used during subsequent procedures.

Another known device for applying electrical current to a blood vessel is described in U.S. Pat. No. 6,050,996 to Schmaltz, et al. (Schmaltz). Schmaltz describes a specialized forceps device that includes modified jaws having a mechanical interface or socket. The forceps device also includes electrodes that are designed with a particular interface or socket configuration that mates with or snaps into the mechanical interface or socket of the jaws. Wires extending from the electrodes are used to deliver current to the tissue.

The interface/socket design described by Schmaltz may allow electrodes to be replaced after each use, but such devices have a number of limitations and disadvantages. Significantly, users are required to purchase a special forceps that includes the sockets and, in addition, required to purchase special electrodes that include sockets capable of mating with the sockets. Thus, the types of forceps and electrodes that can be used are limited. Further, the device describe by Schmaltz is not suitable for converting known and widely used mechanical forceps devices into electro-surgical devices. Rather, such specialized devices serve as more expensive replacement devices with which only certain replacement electrode components can be used.

Another known device for configuring a forceps as a coagulation device is described in U.S. Publication No. 2003/0158549 A1 to Swanson ("Swanson"), the contents of which are incorporated herein by reference. Devices described by Swanson include clamp and base members including an energy transmission device that applied to a clamp member by interfacing mating structures. Swanson describes base members having an aperture for receiving an end of a clamp member inside the base member, and certain described devices include other apertures and holes inside the base member through which wires are placed, and a temperature sensor within the base member. These types of structural configurations and additional components may complicate the design and manufacture of devices.

Accordingly, it would be desirable to have an electro-surgical device, such as an electro-surgical forceps, that can apply electrical current to a localized, targeted area. Further, it would be advantageous to have this ability while using less power. It would also be desirable to have the ability to adapt or convert standard, widely used mechanical forceps or other devices for use in electro-surgery. It would also be desirable to provide electro-surgical attachments that can adapt or convert standard mechanical forceps into electro-surgical devices that are easy to apply, easy to remove, cost effective, replaceable and disposable. These improvements would allow forceps attachments to be discarded after use and new attachments to be applied for subsequent procedures. These improvements would also prevent previously used attachments that may have damaged electrodes from being repeatedly used, thereby improving vessel cauterization and sealing results. This also ensures that new, sterile attachments are used, thereby eliminating the need to re-sterilize components that were used during a previous procedure. It would also be beneficial to have forceps with electro-surgical capabilities without having to purchase specialized forceps devices and specialized electrodes having mating mechanical interfaces.

SUMMARY

In one embodiment, an attachment for converting a mechanical surgical instrument having first and second members coupled at a pivot into an electro-surgical instrument includes a non-conductive sheath and an electrically conductive element. The non-conductive sheath defines a single pocket or cavity and an opening at only one end thereof, and the electrically conductive element that is associated with an outer surface of the sheath. A proximal end of the cover element is slidable over the distal end of a member of the mechanical surgical instrument by inserting the distal end of the member into the pocket or cavity.

In another embodiment, a disposable electro-surgical attachment that includes first and second cover elements can be used for converting a mechanical surgical instrument having first and second members into an electro-surgical instrument. Each cover element includes a non-conductive sheath defining a single pocket, an electrically conductive element attached to an outer surface of the sheath, and a wire. The wire extends from the electrically conductive element, and no portion of the wire is within the sheath. A proximal end of the first cover element is slidable over a distal end of a first member by inserting the distal end of the first member into the pocket of the sheath of the first cover element, and a proximal end of the second cover element is slidable over a distal end of a second member by inserting the distal end of the second member into the pocket of the sheath of the second cover element. Each cover element is free of an open slot formed within the sheath.

In a further embodiment, a surgical instrument that is adapted to apply electrical energy to tissue includes first and second members that are coupled at a pivot and first and second cover elements, a first cover element applied over a distal end of the first member; and a second cover element applied over a distal end of the second member. Each cover element includes a non-conductive sheath defining a single pocket and an electrically conductive element associated with an outer surface of the sheath. A proximal end of the cover element is slidable over the distal end of a member of the mechanical surgical instrument by inserting the distal end of the member into the pocket.

In a further embodiment, a surgical instrument adapted to apply electrical energy to tissue includes first and second members coupled at a pivot, at least one member being moveable about the pivot, and first and second cover elements. Each cover element is slidably applied over a distal end of a member, and includes a non-conductive sheath defining a single pocket, an electrically conductive element attached to an outer surface of the sheath, and a wire. The wire extends from the electrically conductive element, and no portion of the wire is within the sheath. A proximal end of the first cover element is slidable over a distal end of a first member by inserting the distal end of the first member into the pocket of the sheath of the first cover element, and a proximal end of the second cover element is slidable over a distal end of a second member by inserting the distal end of the second member into the pocket of the sheath of the second cover element. Each cover element is free of an open slot formed within the sheath In one or more embodiments, the cover elements are disposable, and the sheath is slidably applied to and slidably removable from a distal end of a member, and can remain attached to the distal end of the member by friction. In one or more embodiments, the sheath has a shape such that it includes a non-conductive arcuate section and a linear section joining ends of the arcuate section. The electrically conductive element can be attached to or embedded within an outer surface of the sheath, e.g., the linear section. In one or more embodiments, the sheath defines a single cavity or pocket and a single opening an end thereof so that a distal tip of a member, when inserted into the pocket or cavity, is surrounded by the sheath and not exposed to the environment. Thus, the sheath does not include any other apertures or holes, does not include an open slot or components such as a temperature sensor. Further, a wire extends from the electrically conductive element outside the sheath so that no portion of the wire is within the sheath. A cover element and member of an instrument are also free of a connector or mechanical interface for attaching a cover element to the member.

Other aspects of embodiments are described herein and will become apparent upon reading the following detailed description with reference to the accompanying drawings.

BRIEF DESCRIPTION OF THE DRAWINGS

Referring now to the drawings in which like reference numbers represent corresponding parts throughout, and in which.

DETAILED DESCRIPTION OF ILLUSTRATED EMBODIMENTS

Figure 1:
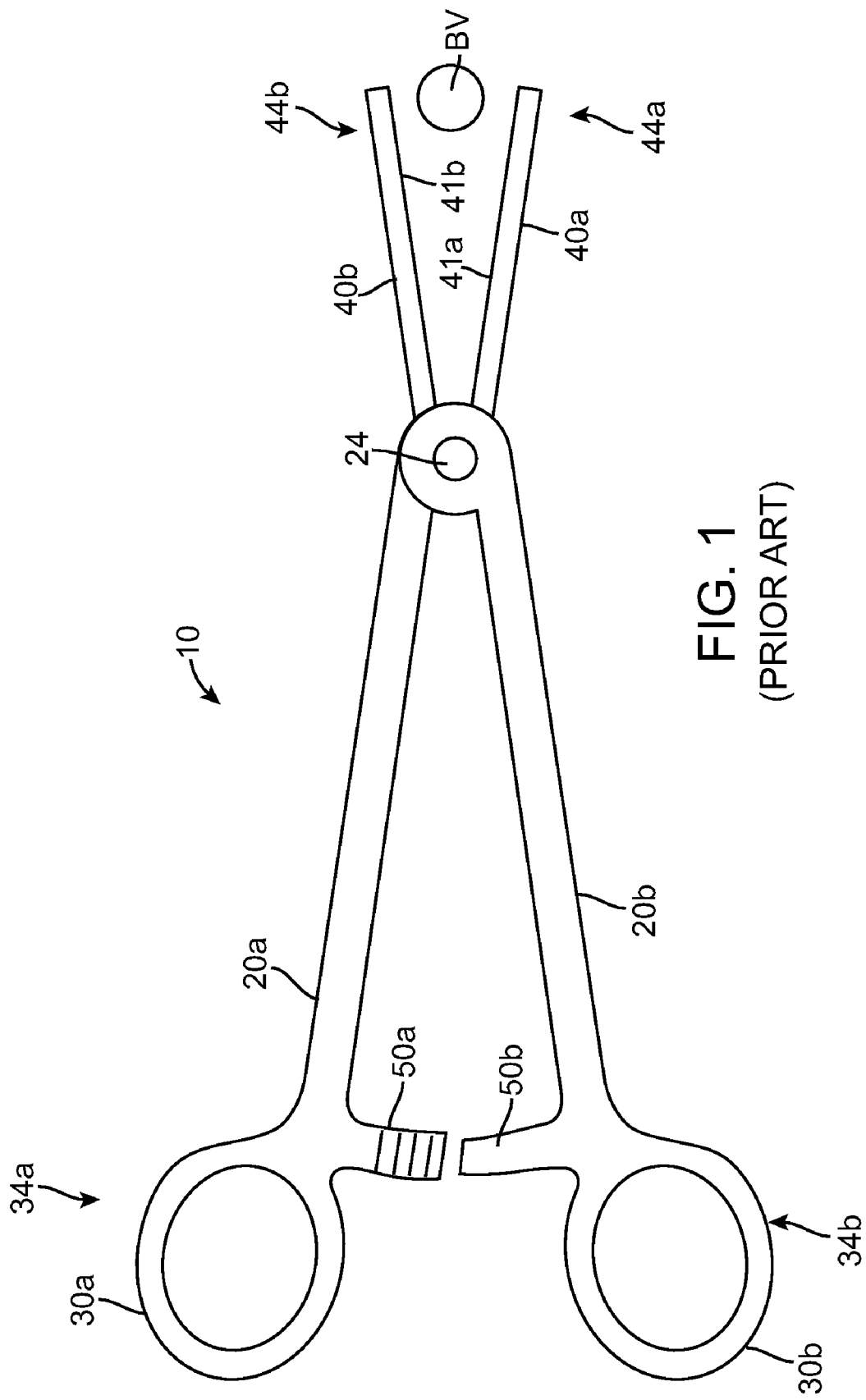
FIG. 1 generally illustrates a known mechanical forceps.

Referring to FIGS. 5-8, according to one embodiment, a replaceable and disposable cover element 500 is configured to be removably attachable or releasably securable to an end of a mechanical surgical instrument, by sliding the cover element 500 over an end of the surgical instrument, thereby adapting the mechanical surgical instrument for electro-surgery. One example of a mechanical surgical instrument that can be converted into an electro-surgical instrument is a forceps, such as the forceps 10 shown in FIG. 1.

Figure 2:
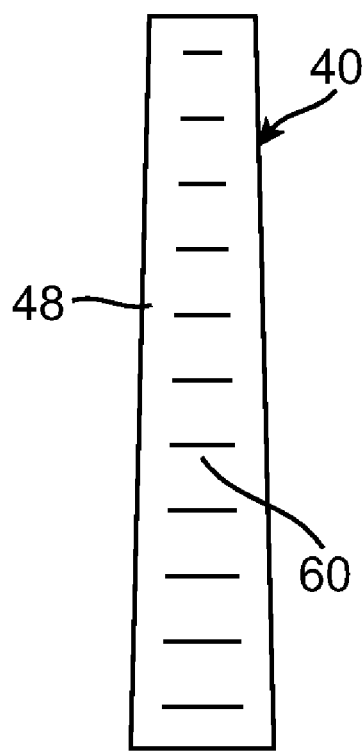
FIG. 2 generally illustrates a straight jaw member of a known forceps.
Figure 3:
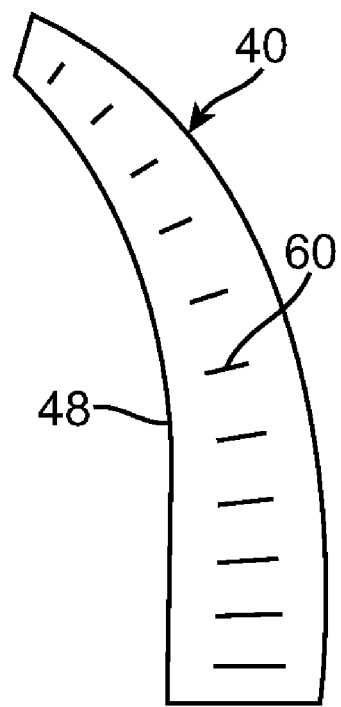
FIG. 3 generally illustrates a curved jaw member of a known forceps.
Figure 4:
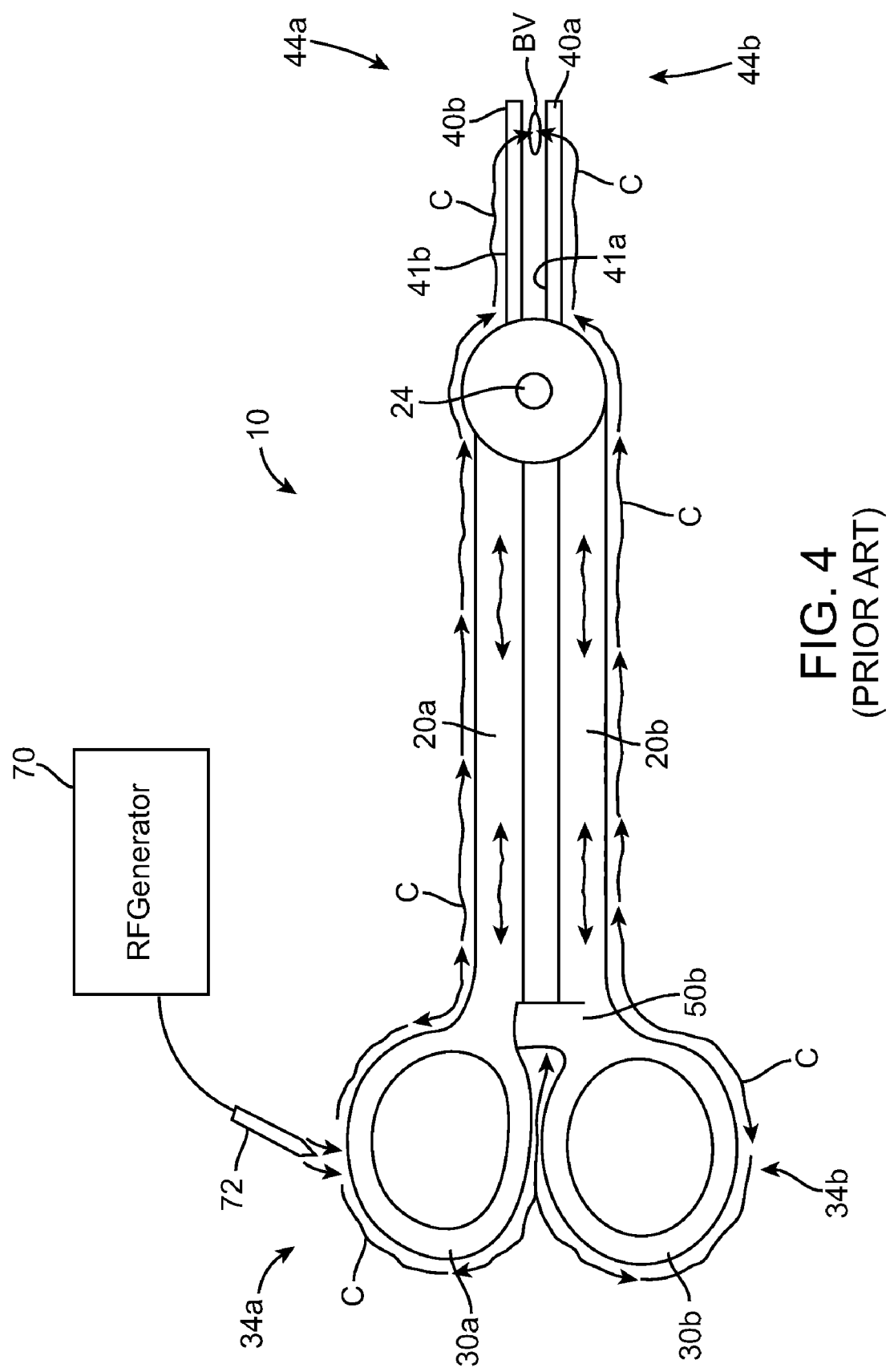
FIG. 4 generally illustrates a known forceps in a closed position and tapping a forceps with an electrical lead to apply electrical current to the forceps.

It should be understood, however, that embodiments can be used with other mechanical surgical instruments and other types of forceps. For example, embodiments can be applied to forceps having distal ends or jaws 40 shaped as shown in FIGS. 2 and 3. Further, although embodiments are described with reference to a forceps having two moveable rigid shaft members 20a and 20b and two moveable rigid jaws 40a and 40b, embodiments can be applied to a surgical instrument or forceps in which one shaft member or one jaw is fixed, and the other shaft member or jaw can be adjusted. Further, embodiments can be applied to adapt scissors-like surgical tools for electro-surgery. Additionally, although embodiments are described with reference to treating a blood vessel, embodiments can be used to treat various types of tissue, such as liver, heart and brain tissue. Accordingly, this specification describes embodiments applied to or including a forceps 10 for grasping a blood vessel as one example of how embodiments can be implemented.

Figure 5:
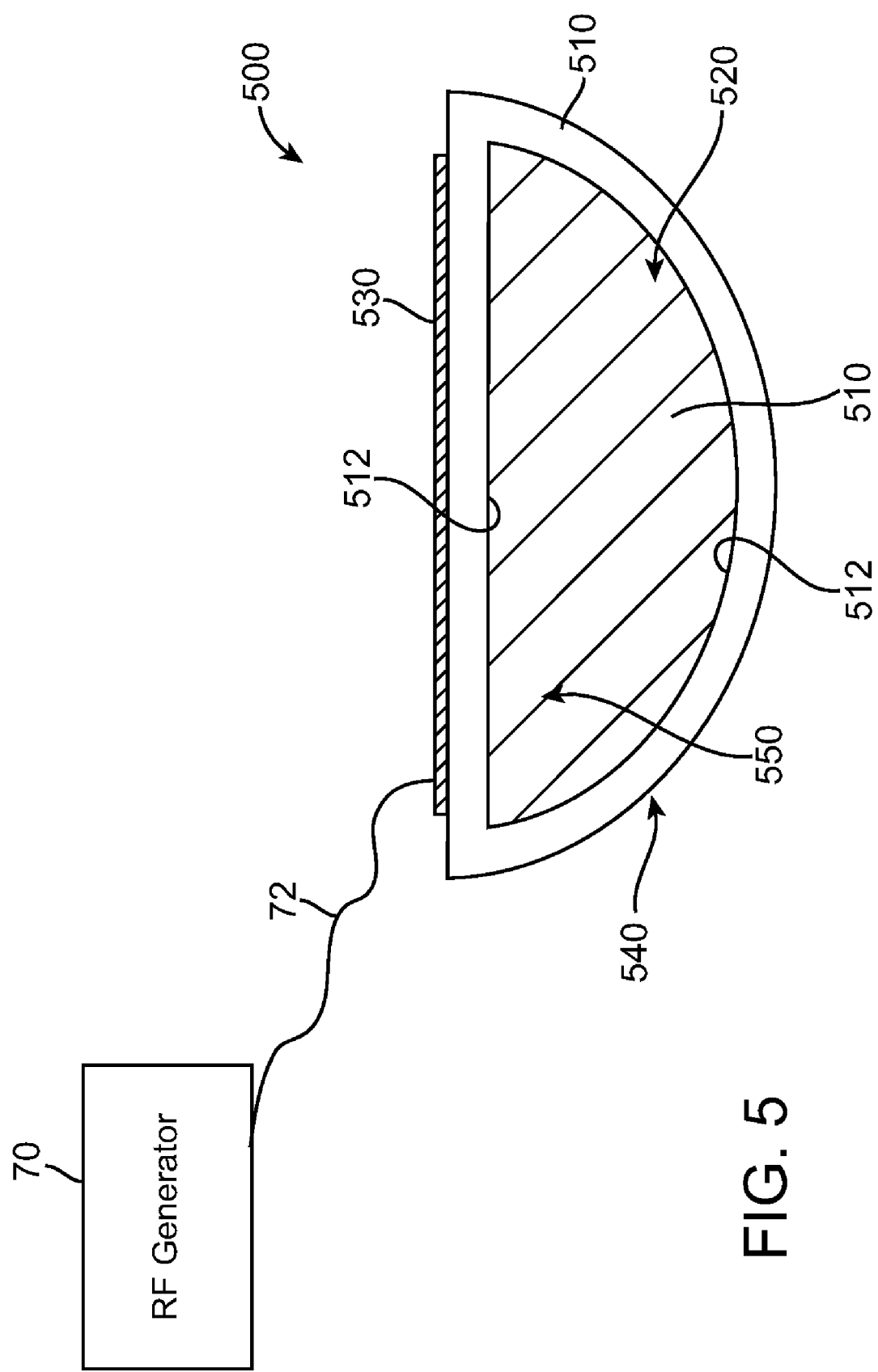
FIG. 5 is a front or proximal end view of a disposable cover element or attachment that is removably secured to a distal end of a member of a surgical device according to one embodiment.
Figure 6:
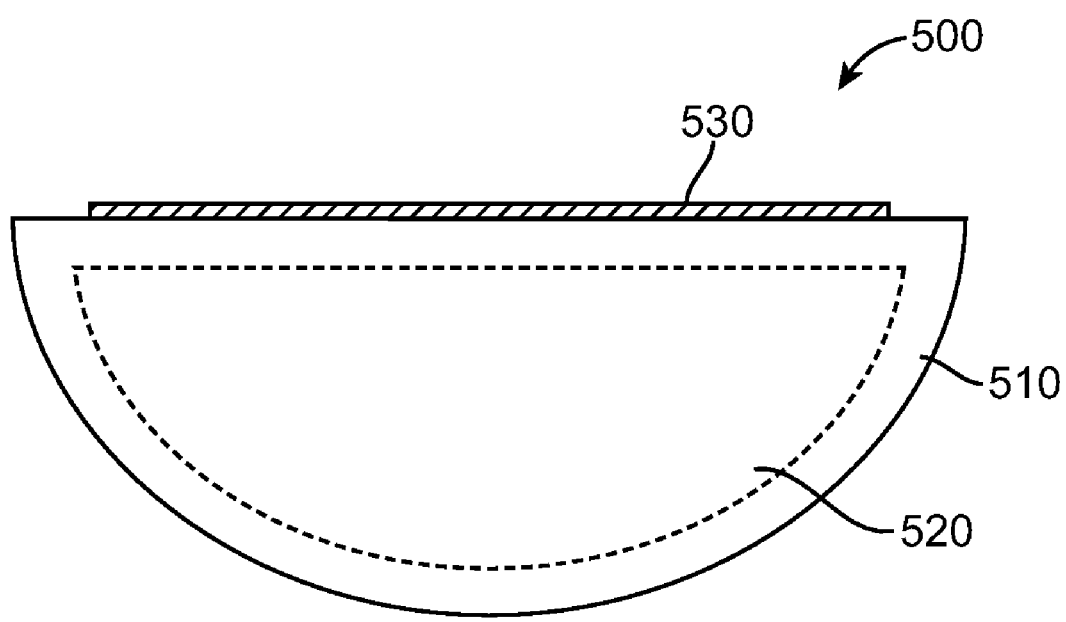
FIG. 6 is rear or distal end view of the disposable cover element shown in FIG. 5.
Figure 7:
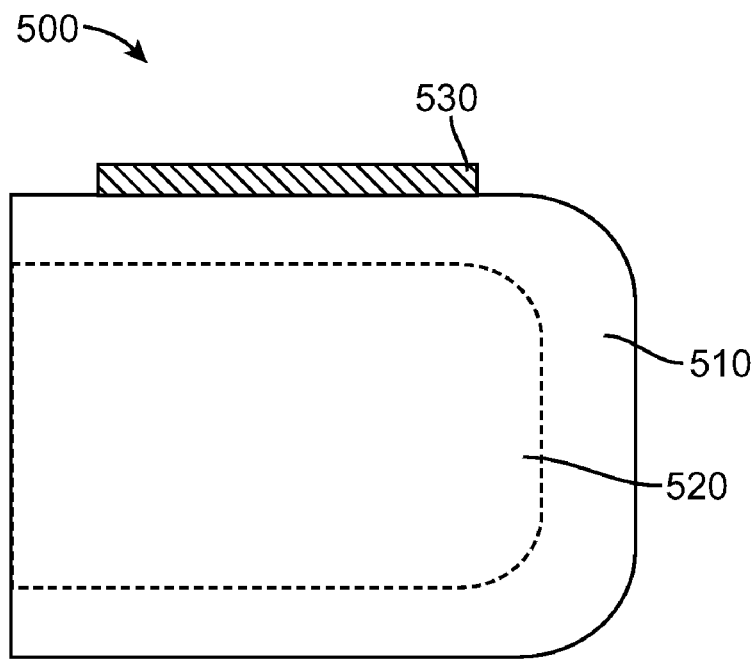
FIG. 7 is a side view of the disposable cover element shown in FIG. 5.
Figure 8:
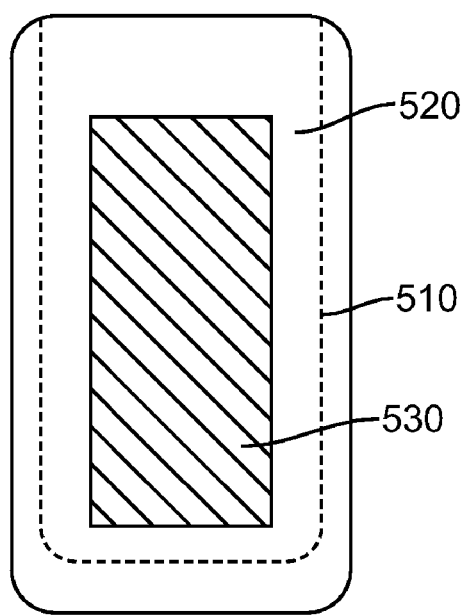
FIG. 8 is a top view of the disposable cover element shown in FIG. 5.

Referring to FIG. 5, a disposable cover element or attachment 500 constructed in accordance with one embodiment includes an outer body or sheath 510 (generally referred to as "sheath 510") that defines a single cavity or pocket 520 (generally referred to as "pocket 520"). Thus, the sheath 510 has a single opening at a proximal end thereof. The pocket 520 does not extend through the distal end of the sheath 510. The sheath 510 does not include an aperture or hole at both of the proximal and distal ends and does not include an open slot or a slot that runs along a length of the sheath 510. Thus, the pocket 520 is a "closed" pocket in that it has only a single opening, and a distal end of a surgical instrument is inserted into the pocket 520 and surrounded by the sheath 510. With this configuration, no outer surface of the distal end of the instrument that is inserted within the pocket 520 is exposed to the environment outside of the sheath 510.

The cover element or attachment 500 also includes an electrically conductive surface or electrode 530 (generally referred to as "electrode 530"). The electrode 530 is affixed to or embedded within an outer surface of the sheath 510. The sheath 510 can be an insulative or non-conducting material, such as a thermo-plastic. In the illustrated embodiment, a cover element 500 is applied over a distal end 44 of each jaw 40 of a forceps 10, and electrical current conducts through the electrodes 530 and is applied locally to a blood vessel or other tissue held between the electrodes 530. Thus, embodiments advantageously reduce conduction of current to other forceps 10 components and surrounding tissue and focus application of current to target tissue.

Figure 9:
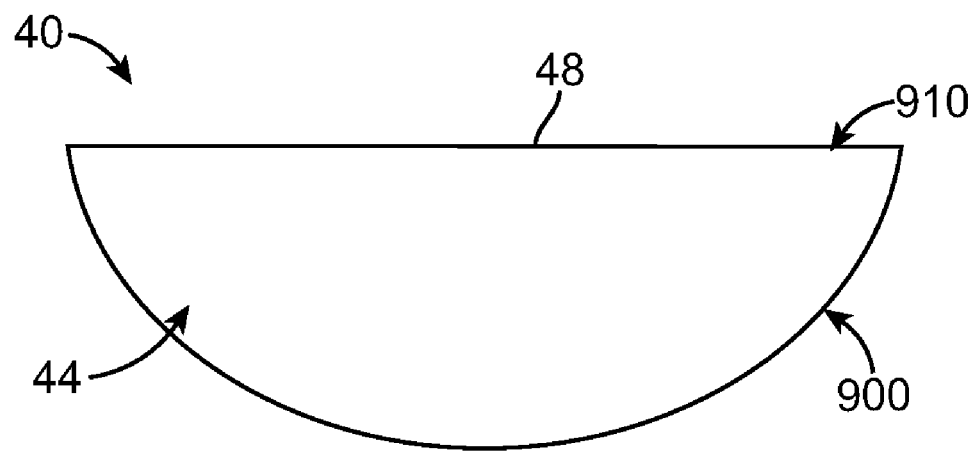
FIG. 9 is a cross-sectional view of a jaw member to which a cover element can be attached according to one embodiment.
Figure 10:
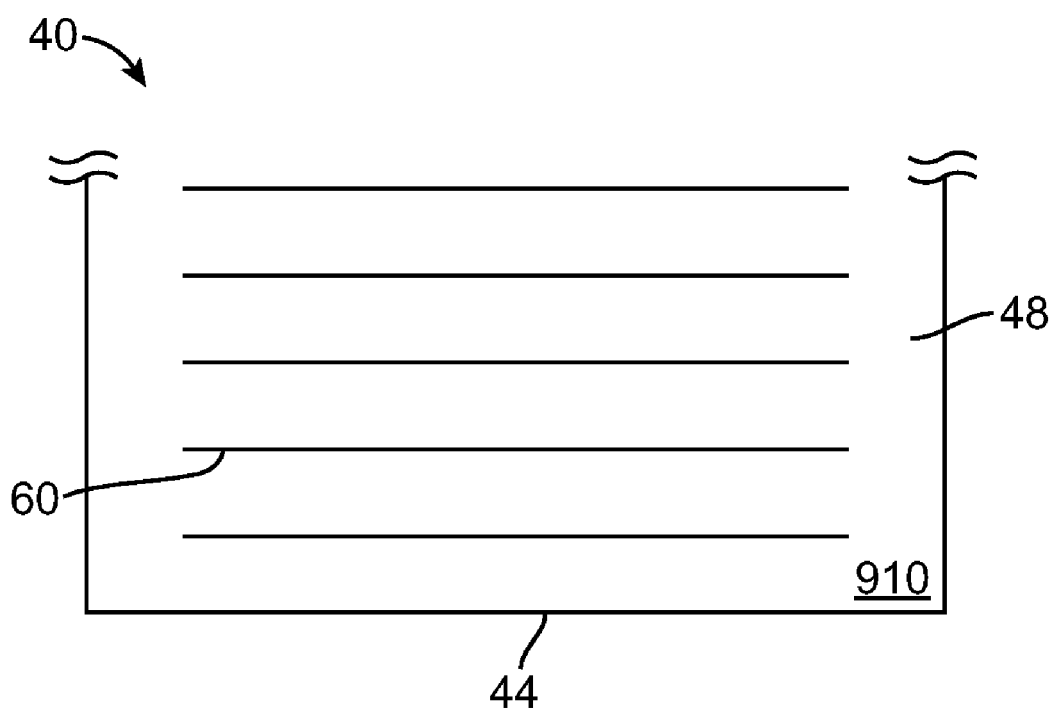
FIG. 10 is a partial top view of the jaw member shown in FIG. 9.

The cover element 500 has a shape and size so that it can be placed over a distal end 44 of a jaw 40 of a forceps 10. For example, referring to FIGS. 9 and 10, according to one embodiment, a jaw 40 of one known forceps 10 has a "U" or "C" shaped cross-section that includes an arcuate section 900 and a linear section 910 extending across first and second ends of the arcuate section 900. In one embodiment, the sheath 510 defines a single, enclosed pocket 520 that has a corresponding "U" or "C" shaped arcuate section 540 and linear section 550 extending across ends of the arcuate section 540, thereby defining a corresponding "U" or "C" shaped pocket 520. The pocket 520 is of a suitable shape and size so that the cover element 500 can be attached to the jaw 40 by sliding the cover element 500 over the distal end 44 of a jaw 40 by inserting the distal end 44 into the pocket 520. The electrode 530 is attached to the linear section 910, i.e., an outer surface of the cover element 500.

It should be understood that the figures may not be to scale and may not reflect actual sizes and shapes or reflect relative dimensions. Thus, the shapes, dimensions and proportions of the sheath 510, pocket 520 and electrode 530 can vary in practice. Further, it should be understood that the shape and size of a cover element 500 and the dimensions and proportions of the sheath 510, pocket 520 and electrode 530 can vary depending on the shape and dimensions of the jaw 40 or distal tip of the surgical instrument to which the cover element 500 is to be attached. Thus, FIGS. 5-8 are provided to generally illustrate one example configuration of a forceps 10 to which embodiments can be applied.

The sheath 510 is a composed of a suitable non-conductive material and is a suitable shape and size so that friction between an inner surface 512 of the sheath 510 and the outer arcuate and linear sections 900 and 910 of a jaw 40 is sufficient to hold the cover element 500 in place on the jaw 40. The frictional force, however, should be sufficiently low to allow a surgeon to slidably remove the cover element 500 from the jaw 40. For example, a jaw 40 of one known forceps 10 is composed of stainless steel, and the sheath 510 can be composed of a thermo-plastic. According to one embodiment, the dimensions of the pocket 520 are slightly smaller than the outer dimensions of the jaw 40 so that the inner surface 512 of the cover element 500 creates an interference fit with the outer surface of the jaw 40. With this configuration, the flexible sheath 510 grips the jaw 40 and fits tightly on the jaw 40 while still being slidably removable from the jaw 40.

Thus, in contrast to known devices, embodiments utilize a sheath 510 having only a single pocket or opening 520 at one end of the cover element 500, and into which a distal end 44 of a jaw 40 is inserted. Embodiments, therefore, do not require, and do not have, additional slots formed within the sheath 510 for receiving electrically conducting elements since the electrode 530 is attached to an outer surface of the sheath 510. Further, embodiments do not require, and do not have, additional apertures or holes for wires, temperature sensors or other components placed or formed within the body of the sheath 510 since no additional wiring is necessary due to the electrode 530 being attached to an outer surface of the sheath 510. Additionally, embodiments do not require, and do not have, any mating structures or other mechanical components that interface with a jaw since cover elements 500 are slidably applied to and removed from distal ends of a jaw 40.

In this manner, embodiments advantageously provide significant improvements over known devices and allow various mechanical surgical devices including forceps to be converted into electro-surgical devices while simplifying the manner in which these mechanical-to-electrosurgical conversions are made. Embodiments advantageously allow standard mechanical forceps devices that are widely used to be converted into electro-surgical devices in less complicated manner than known devices. FIGS. 11-18 illustrate further aspects of embodiments and how they may be implemented.

Figure 11:
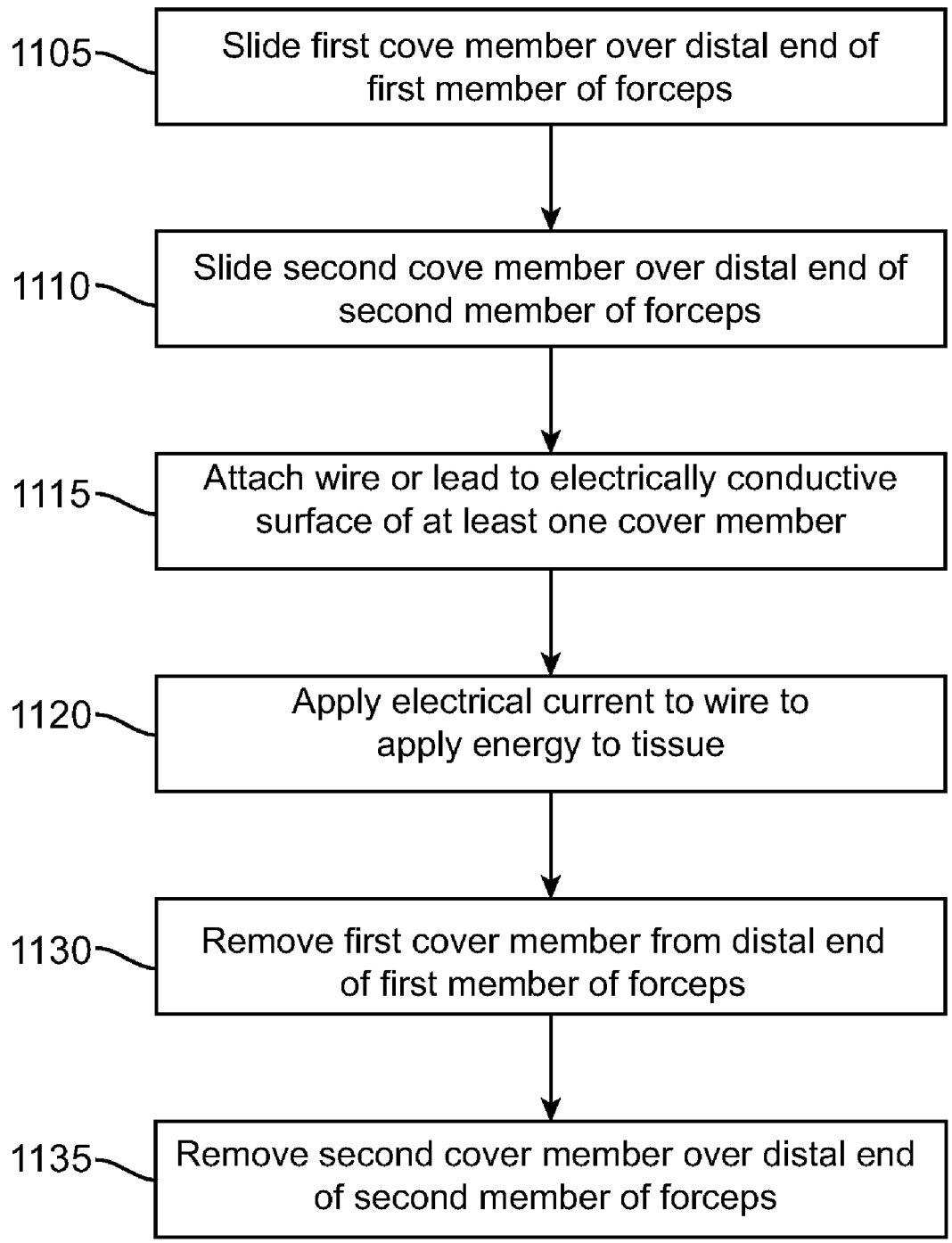
FIG. 11 is a flow chart of a method of performing an electro-surgical procedure according to one embodiment.

Referring to FIG. 11, and with further reference to FIGS. 12-15, a method 1100 of using cover element attachments, such as the attachment 500 shown in FIGS. 5-10, during a surgical procedure includes sliding a first cover element 500*a* over a distal end 44*a* of first jaw 40*a* of a first shaft member 20*a* of the forceps 10 at stage 1105, and sliding a second cover element 500*b* over a distal end 44*b* of a second jaw 40*b* of second member 20*b* of the forceps 10 at stage 1110. At stage 1115, one or more wires or electrical leads 72 are attached to one or both of the electrically conductive surfaces or electrodes 530*a*, 530*b* of the cover elements 500*a*, 500*b* if the wires or leads 72 were not previously attached or in contact with the electrodes 530*a*, 530*b* that are attached or affixed to respective cover elements 500*a*, 500*b*. At stage 1120, one or both of the jaws 20*a*, 20*b* are manipulated by a surgeon to secure a blood vessel or tissue between electrodes 530*a*, 530*b* of the cover elements 500*a*, 500*b*. At stage 1125, electrical current is applied from the RF generator 70 to the wire 72, thereby applying current through the cover element electrodes 530*a*, 530*b* and to the blood vessel or other tissue held between the electrodes 530*a*, 530*b*, thereby cauterizing and/or sealing the blood vessel. After the procedure has been completed, at stage 1130, the jaws 20*a*, 20*b* are released. At stage 1135, the first cover element 500*a* is slidably removed from the distal end of the first jaw 20*a* of the forceps 10, and at stage 1140, the second cover element 500*b* is slidably removed from the distal end of second jaw 20*b* of the forceps 10.

Figure 16:
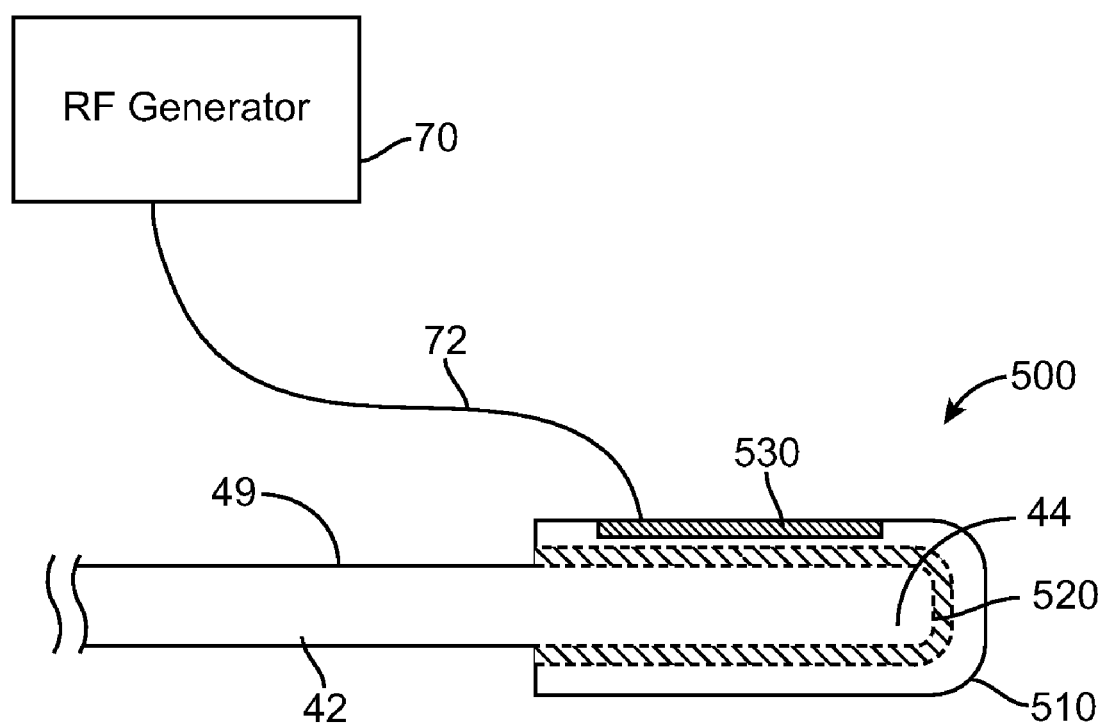
FIG. 16 illustrates a disposable cover element or attachment having an electrically conductive surface or electrode embedded within a non-conductive body according to one embodiment.

FIGS. 12-15 illustrate an electrode 530 that is affixed to or placed on an outer surface of the sheath 510. Referring to FIG. 16, in an alternative embodiment, the electrically conductive surface or electrode 530 can be embedded or integrated within the sheath 510. In both configurations, the electrode 530 is attached to an outer surface of the sheath 510 so that the electrode 530 surface is exposed, and it is not necessary to slide an electrode through a slot formed in the sheath 510. Thus, it is also not necessary to run wires inside the sheath 510 or through holes or apertures formed in the sheath 510 to house electrode 530 wiring.

Figure 12:
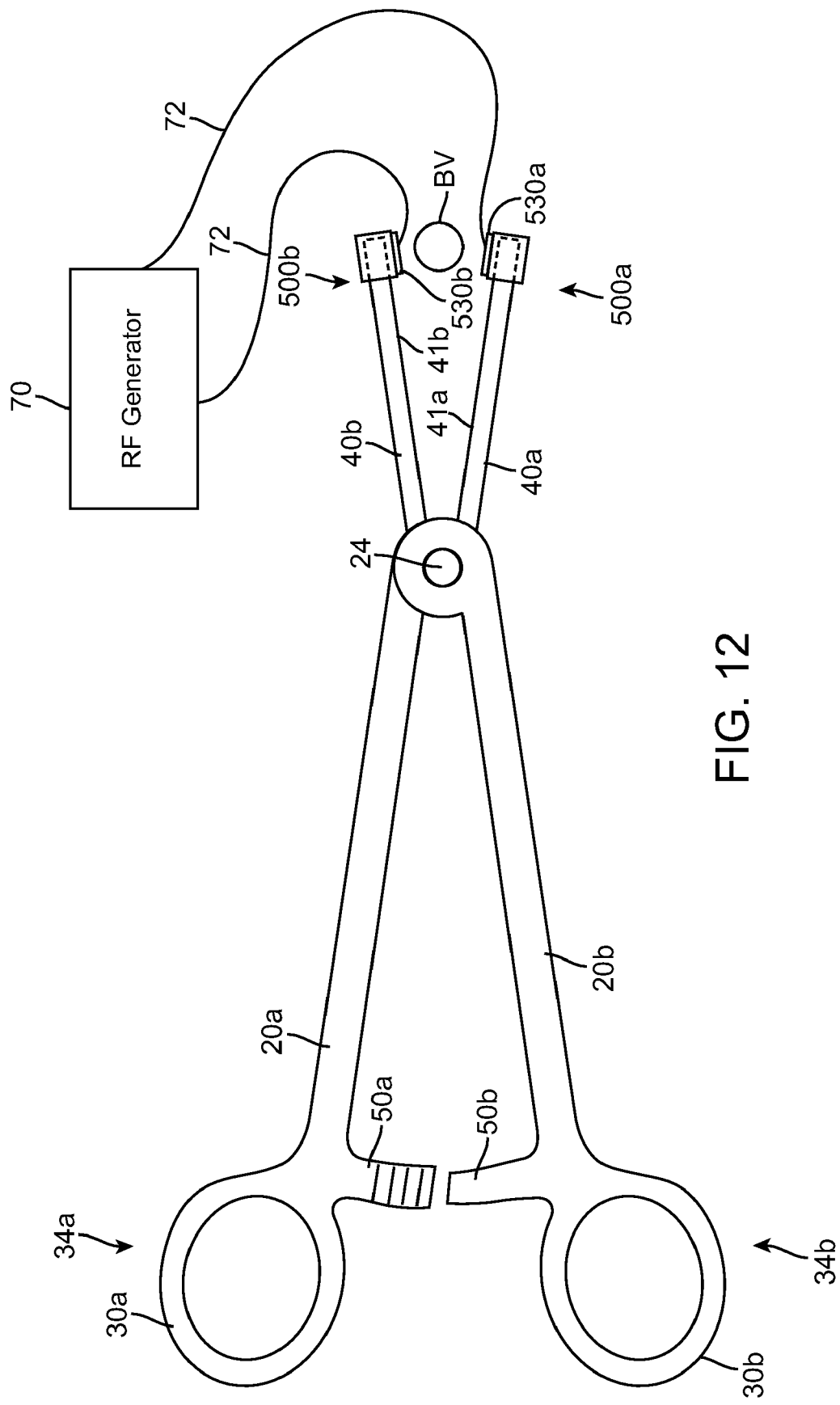
FIG. 12 illustrates two disposable cover elements attached to distal ends of jaws of a forceps according to one embodiment.
Figure 13:
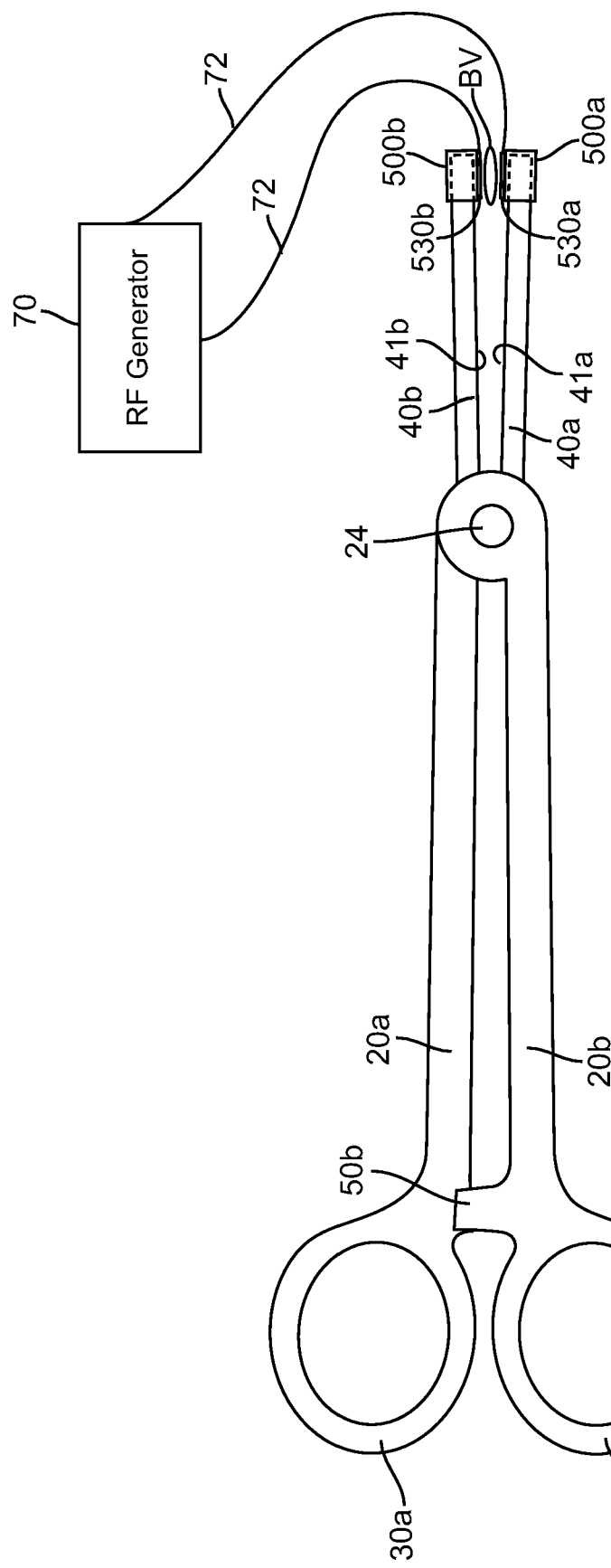
FIG. 13 illustrates the forceps shown in FIG. 12 grasping a blood vessel.
Figure 14:
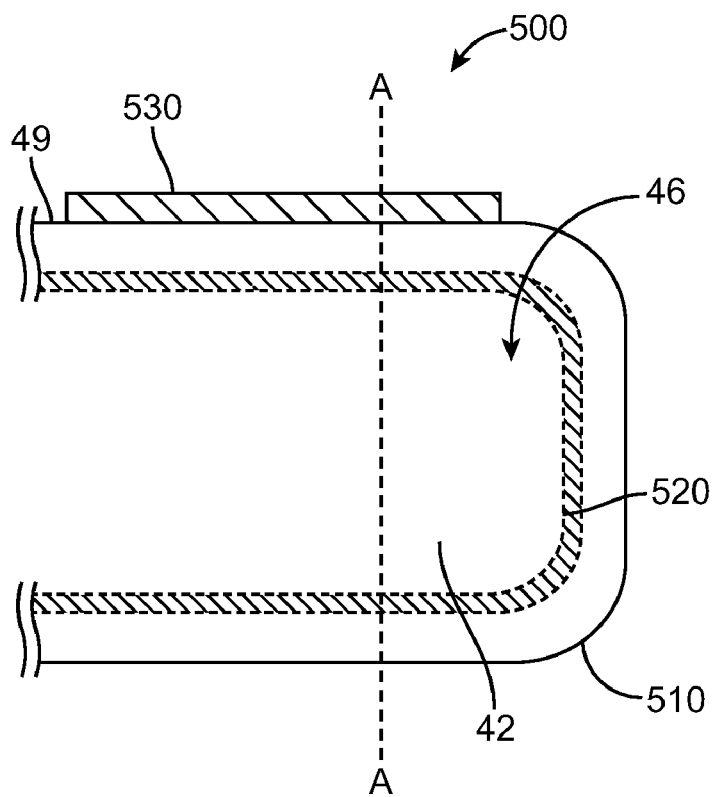
FIG. 14 is a side view further illustrating how a cover element is applied over a distal end of a forceps according to one embodiment.
Figure 15:
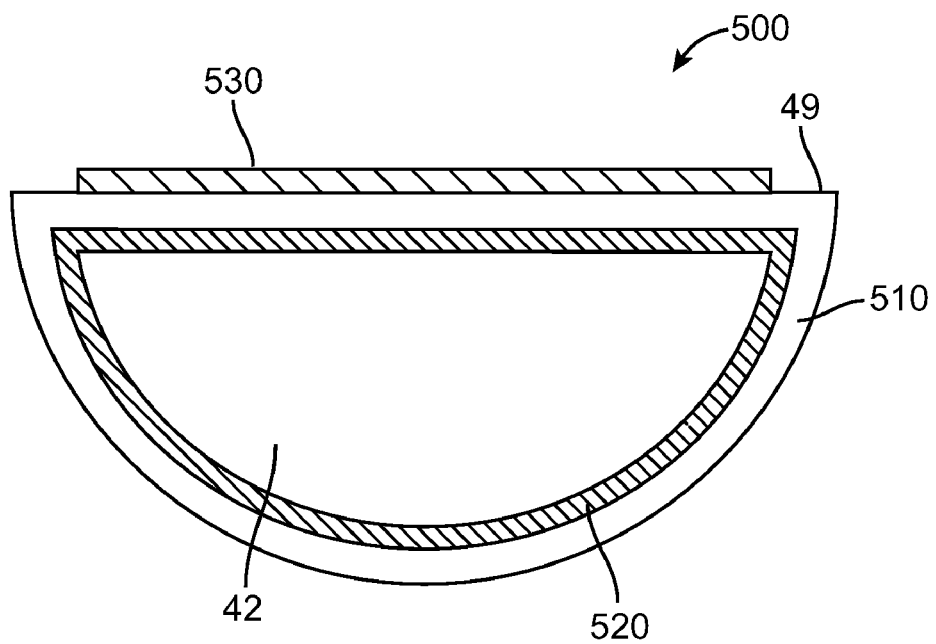
FIG. 15 is a cross-sectional view of FIG. 14 along line A-A.

It should be understood that the shape and size of the electrode 530, and how much of the outer surface of the sheath 510 should be covered by an electrode 530 may vary depending on the particular application and surgical needs. Accordingly, FIGS. 12-15, which illustrate electrically conductive surfaces 530 as being surfaces that engage a blood vessel, are provided to show one example of how embodiments can be implemented. Further, although FIGS. 12 and 13 illustrate wire or leads 72 extending directly from the generator 70 to the electrode 530 of the cover element 500, other wiring configurations can also be utilized. For example, wires or leads 72 can run along or through one or more forceps components, such as the pivot 24.

Illustrated embodiments are configured as bipolar electro-surgical forceps having a cover element 500 applied over each jaw 40. Alternative embodiments can be implemented as monopolar devices that use only one cover element 500 rather than two cover elements 500 with opposing or adjacent electrodes 530 as shown in the Figures. As with bipolar devices, the wires or leads 72 are electrically coupled between the RF generator 70 and an electrically conducting surface 530 of a first cover element 500 applied over one of the jaws 40. When the generator 70 is activated, electrical current is conducted from the generator 70, through the lead 72, through the electrically conductive surface 530 of the cover element 500 and through the blood vessel to be treated. Electrical current then conducts through the patient to a "return" electrode (not shown) that is positioned in contact with the skin of the patient. Whether arranged in a monopolar or bipolar fashion, a forceps 10 can be configured to cauterize the blood vessel or seal the blood vessel using a cover element 500 having a sheath 510 defining a single pocket and an electrode 530 attached to an outer surface of the sheath 510. The current can be adjusted as necessary to provide the desired cauterization or sealing capabilities.

Embodiments significantly improve upon known forceps and known devices to transform forceps into electro-surgical instruments by applying electrical current to a localized, selected area between the forceps tips. Embodiments advantageously utilize lower current and power levels to cauterize or seal a vessel since current is not conducted globally to other areas that do not require treatment. Further, embodiments allow standard, widely used forceps 10 to be configured for electro-surgery using cover elements or attachments 500 that can slide on and slide off of the tips of the forceps 10. Embodiments facilitate single use of electrodes 530 since cover elements 500 are disposable, thereby preventing re-use of electrodes that might be damaged and eliminating the need to sterilize electrodes. Further, embodiments advantageously allow cover elements 500 to be removed and discarded after each procedure so that the forceps 10 can be used for their original intended purpose or for additional electro-surgical procedures using new cover elements 500. Additionally, the cost of manufacturing and using cover elements 500 is reduced compared to other known devices that use base members that define multiple slots, apertures or holes for receiving electrically conductive elements, wires or temperature sensors. Further, with embodiments, it is not necessary to modify contact surfaces of forceps or integrate mechanical interfaces or sockets into the contact surfaces or modify electrodes to have mating interfaces or sockets. Thus, embodiments advantageously allow various surgical instruments and various forceps to be adapted for use with electro-surgical applications.

Although particular embodiments have been shown and described, it should be understood that the above description is not intended to limit the scope of embodiments since various changes and modifications may be made without departing from the scope of the claims. Thus, embodiments are intended to cover alternatives, modifications, and equivalents that fall within the scope of the claims.

What is claimed is:

1. A disposable attachment for converting a mechanical surgical instrument having first and second members coupled at a pivot into an electro-surgical instrument, the attachment comprising:
   a first cover element; and
   a second cover element,
   each cover element including
      a non-conductive sheath defining a single pocket, wherein an outer surface of the sheath comprises a D-shaped cross-section having an arcuate section and a linear section,
      an electrically conductive element having a bottom surface directly attached to the linear section of the outer surface of the sheath, and
      a wire extending from the electrically conductive element, wherein no portion of the wire is within the sheath, a proximal end of the first cover element is slidable over a distal end of a first member by inserting the distal end of the first member into the pocket of the sheath of the first cover element, and a proximal end of the second cover element is slidable over a distal end of a second member by inserting the distal end of the second member into the pocket of the sheath of the second cover element, and each cover element is free of an open slot formed within the sheath.

2. The attachment of claim 1, wherein each sheath is slidably removable from the distal end of a member.

3. The attachment of claim 1, wherein each sheath remains attached to the distal end of a member by friction between an inner surface of the sheath and an outer surface of the distal end of the member.

4. The attachment of claim 1, wherein each sheath is configured so that a distal tip of a member is surrounded by the sheath when the distal tip is inserted into the pocket of the sheath.

5. The attachment of claim 1, wherein each pocket is substantially the same shape and size as a distal end of a member.

6. The attachment of claim 1, wherein each sheath is free of other holes or cavities other than the single pocket defined by each sheath.

7. The attachment of claim 1, wherein each sheath is free of a temperature sensor.

8. A surgical instrument adapted to apply electrical energy to tissue, comprising:
    first and second members coupled at a pivot, at least one member being moveable about the pivot;
    a first cover element applied over a distal end of the first member; and
    a second cover element applied over a distal end of the second member,
    each cover element having a non-conductive sheath defining a single pocket, and an electrically conductive element associated with an outer surface of the sheath, wherein a proximal end of the first cover element is slidable over the distal end of the first member by inserting the distal end of the first member into the pocket of the sheath of the first cover element,
    wherein the outer surface of each sheath comprises a D-shaped cross-section having an arcuate section and a linear section, and
    wherein a bottom surface of each electrically conductive element is directly attached to the linear section of the outer surface of one of the sheaths.

9. The instrument of claim 8, wherein each sheath is free of any other internal components or structures.

10. The instrument of claim 8, wherein the first and second cover elements are disposable.

11. The instrument of claim 8, wherein each member is free of a connector or mechanical interface for attaching a cover element to the member.

12. The instrument of claim 8, wherein the surgical instrument is a forceps.

13. The instrument of claim 8, wherein each cover element remains attached to a distal end of a member by friction between an inner surface of a sheath and an outer surface of the distal end of the member.

14. The instrument of claim 8, wherein each sheath is configured so that a distal tip of a member is surrounded by the sheath when the distal tip is inserted into the pocket.

15. The instrument of claim 8, wherein each sheath is free of an open slot.

16. The instrument of claim 8, wherein each sheath is free of other holes or cavities other than the single pocket defined by each sheath.

17. The instrument of claim 8, wherein each sheath is free of a temperature sensor.

18. A surgical instrument adapted to apply electrical energy to tissue, comprising:
    first and second members coupled at a pivot, at least one member being moveable about the pivot;
    a first cover element slidably applied over a distal end of the first member; and
    a second cover element slidably applied over a distal end of the second member,
    each cover element including
        a non-conductive sheath defining a single pocket, wherein an outer surface of the sheath comprises a D-shaped cross-section having an arcuate section and a linear section,
        an electrically conductive element having a bottom surface directly attached to the linear section of the outer surface of the sheath, and
        a wire extending from the electrically conductive element, wherein no portion of the wire is within the sheath, a proximal end of the first cover element is slidable over the distal end of the first member by inserting the distal end of the first member into the pocket of the sheath of the first cover element, and a proximal end of the second cover element is slidable over the distal end of the second member by inserting the distal end of the second member into the pocket of the sheath of the second cover element, and each cover element is free of an open slot formed within the sheath.

19. The instrument of claim 18, wherein the first and second cover elements are disposable.

20. The instrument of claim 18, wherein each member is free of a connector or mechanical interface for attaching a cover element to the member.

21. The instrument of claim 18, wherein the surgical instrument is a forceps.

22. The instrument of claim 18, wherein each cover element remains attached to a distal end of a member by friction between an inner surface of a sheath and an outer surface of the distal end of the member.

23. The instrument of claim 18, wherein each sheath is configured so that a distal tip of a member is surrounded by the sheath when the distal tip is inserted into the pocket of the sheath.

24. The instrument of claim 18, wherein each sheath is free of other holes or cavities other than the single pocket defined by each sheath.

25. The instrument of claim 18, wherein each sheath is free of a temperature sensor.

* * * * *